United States Patent [19]
Wong et al.

[11] Patent Number: 5,171,526
[45] Date of Patent: Dec. 15, 1992

[54] OPHTHALMIC COMPOSITIONS AND METHODS FOR PRESERVING AND USING SAME

[75] Inventors: Michelle P. Wong, Tustin; Anthony Dziabo, El Toro, both of Calif.

[73] Assignee: Allergan, Inc., Irvine, Calif.

[21] Appl. No.: 461,161

[22] Filed: Jan. 5, 1990

[51] Int. Cl.$^5$ .................. A61L 2/18; A01N 33/12
[52] U.S. Cl. ..................... 422/28; 514/840; 514/642; 424/78.04
[58] Field of Search ............... 422/28, 32; 514/642–643, 839, 840; 424/78, 70, 78.04; 134/901

[56] References Cited

U.S. PATENT DOCUMENTS

| | | | |
|---|---|---|---|
| Re. 32,672 | 5/1988 | Huth et al. | 252/95 |
| 3,771,989 | 11/1973 | Pera et al. | 514/642 |
| 3,874,870 | 4/1975 | Green et al. | 514/642 |
| 3,910,296 | 10/1975 | Karageozian et al. | 134/2 |
| 3,912,451 | 10/1975 | Gaglia, Jr. | 422/30 |
| 4,025,617 | 5/1977 | Green et al. | 424/78 |
| 4,168,112 | 9/1979 | Ellis et al. | 351/160 |
| 4,250,269 | 2/1981 | Buckman et al. | 524/236 |
| 4,443,429 | 3/1984 | Smith et al. | 424/78 |
| 4,499,077 | 2/1985 | Stockel et al. | 514/642 |
| 4,525,346 | 6/1985 | Stark | 514/642 |
| 4,654,208 | 3/1987 | Stockel et al. | 514/642 |
| 4,783,488 | 11/1988 | Ogunbiyi et al. | 514/635 |
| 4,786,436 | 11/1988 | Ogunbiyi et al. | 252/352 |
| 4,908,209 | 3/1990 | McIntosh et al. | 424/78 |
| 4,935,232 | 6/1990 | McIntosh | 424/78 |

OTHER PUBLICATIONS

The Buckman Toxicity Profile, Memphis, Tenn., Jul. 25, 1984.
The Buckman Technical Specifications, Memphis, Tenn., Sep. 23, 1981.
The Buckman Material Safety Data Sheet, Memphis, Tenn., Oct. 16, 1986.
The Lens Care Research Bulletin Bausch and Lomb.
The Croda, Inc. Bulletin–Crodacel Q (LM&S), Jun. 24, 1986.
The Croda, Inc. Bulletin–Croquat L, Oct. 16, 1982.
The Croda, Inc. Material Safety Data Sheet (lauroyl quaternized hydroxyethyl cellulose), New York, N.Y., Jan. 22, 1987.
The Croda, Inc. Material Safety Data Sheet (cocoyl quaternized hydroxyethyl cellulose), New York, N.Y. Jan. 22, 1987.
The Croda, Inc. Material Safety Data Sheet (stearoyl quaternized hydroxyethyl cellulose), New York, N.Y., Jan. 22, 1987.

*Primary Examiner*—Robert J. Warden
*Assistant Examiner*—Theresa A. Trembley
*Attorney, Agent, or Firm*—Gordon L. Peterson; Frank J. Uxa, Jr.

[57] ABSTRACT

Ophthalmic compositions, such as those used to care for contact lenses, methods of preserving such compositions, and methods for disinfecting contact lenses using such compositions are disclosed. The compositions may comprise an ophthalmically acceptable, liquid aqueous medium and, included therein, an effective preserving or disinfecting amount of an ophthalmically acceptable quaternary ammonium substituted matrix material, the matrix material being selected from the group consisting of proteinaceous materials, carbohydrate materials and mixtures thereof.

66 Claims, No Drawings

5,171,526

OPHTHALMIC COMPOSITIONS AND METHODS FOR PRESERVING AND USING SAME

BACKGROUND OF THE INVENTION

This invention relates to ophthalmic compositions and methods for preserving and using such compositions. More particularly, the present invention relates to ophthalmic compositions, e.g., useful in caring for contact lenses, which include one or more quaternary ammonium substituted matrix materials, e.g., as preservatives or disinfectants, and to methods for disinfecting and/or preserving using such compositions.

Various compositions, e.g., solutions, are used in association with contact lenses to ensure that the lenses may be safely, comfortably and conveniently worn. Contact lens care compositions, for example, disinfecting compositions, preserving compositions, cleaning compositions, wetting compositions, conditioning compositions and the like, often utilize at least one disinfectant or preservative, depending on the type of composition, for disinfecting or preserving contact lenses after wear or preserving the lens care composition itself. A contact lens disinfecting composition generally has sufficient antimicrobial activity so that when the composition is contacted with a lens to be disinfected, microorganisms associated with the lens are killed or otherwise removed and the contact lens is effectively disinfected within a reasonable time, e.g., in the range of about 0.1 hour to about 12 hours. A contact lens disinfecting composition may be termed a microbio-cidal composition. In contrast, a contact lens preserving composition has sufficient antimicrobial activity, often less of such activity than is present in a contact lens disinfecting composition so that when the composition is contacted with a contact lens substantially no increase in the microorganism population on the lens or in the composition is obtained. A contact lens preserving composition may be termed a microbio-static composition. Other contact lens care compositions are preserved to prevent any substantial increase in, or to gradually decrease, the population of contaminating microorganisms in the compositions and, thereby, to extend their shelf life. Some preservatives used in lens preserving compositions or in preserved compositions may also be used as disinfecting agents in lens disinfecting compositions.

Various compounds are known for use as preserving agents in contacts lens preserving compositions and preserved contact lens care compositions. Examples include thimerosal, benzalkonium chloride and chlorhexidine. However, these preserving agents are known to exhibit ocular toxicity which may result in irritation or sensitivity to the eye. The degree of ocular toxicity increases when these agents are utilized as disinfecting agents. Further, a soft contact lens, a rigid gas permeable contact lens (RGP) or a hard contact lens can absorb or adsorb these compounds. This causes the contact lens to retain the irritating compound and contributes to the eye irritation and sensitivity which may result.

Stark U.S. Pat. No. 4,525,346 discloses a contact lens disinfecting solution and preserved contact lens care compositions containing 1-tris (2-hydroxyethyl) ammonium-2-butenyl-4-poly [1-dimethyl ammonium-2-butenyl]-w-tris (2-hydroxyethyl-) ammonium the salt of which has a pharmaceutically acceptable anion. The quaternary ammonium polymer disclosed in this Stark patent is capable of causing irritation and sensitivity to some contact lens wearers.

Other conventional methods of contact lens chemical disinfection utilize one or more active disinfecting agents in an aqueous medium, for example a chlorhexidine/thimerosal solution or a relatively mild solution of hydrogen peroxide. Some of these disinfecting solutions, such as those named above, are cytotoxic and are known to be adsorbed or absorbed onto or into a contact lens and cause the lens to elicit a cytotoxic response after disinfection. For example, contact lenses which have been soaked in a disinfecting hydrogen peroxide solution are to be treated to remove residual hydrogen peroxide, e.g., by soaking in a catalase solution, before they may be comfortably and safely worn again. If residual hydrogen peroxide remains on the lenses, then irritation or injury to the eye may result.

Thus, it is readily apparent that a continuing need exists for safe and efficacious compositions that can be used as contact lens disinfecting and preserving compositions and as preserved contact lens care compositions.

SUMMARY OF THE INVENTION

New disinfecting and preserving compositions and methods, particularly such compositions and methods directed to contact lens care, have been discovered. The present compositions include effective disinfectants and/or preservatives. Thus, for example, a contact lens can be effectively disinfected in a reasonable length of time. Also, contact lens care products can be effectively preserved against growth of contaminating microorganisms. Importantly, such disinfecting and preserving activities are achieved and the contact lenses disinfected, preserved or otherwise cared for using the present compositions can be safely and comfortably worn with little or no risk of eye irritation or sensitivity.

In one broad aspect of the invention, a composition useful for disinfecting, or preserving, a contact lens is provided. This composition includes an ophthalmically acceptable, preferably sterile, medium, preferably a liquid aqueous medium. Included within this medium is an effective disinfecting, or preserving, amount of an ophthalmically acceptable quaternary ammonium substituted matrix material selected from proteinaceous materials, carbohydrate materials and mixtures thereof. Methods of disinfecting, or preserving, a contact lens include contacting the lens to be disinfected, or preserved, with an appropriate composition, as described herein.

Preserved compositions, e.g., contact lens care compositions include an ophthamically acceptable medium, preferably containing one or more components effective to beneficially affect a contact lens and/or the wearing of a contact lens. Such preserved compositions include an effective preserving amount of an ophthalmically acceptable quaternary ammonium substituted matrix material, as described herein.

DETAILED DESCRIPTION OF THE INVENTION

The present invention is applicable to disinfecting or preserving al types of lenses, e.g., contact lenses, which are benefited by such disinfecting or preserving. Such lenses, e.g., conventional soft contact lenses, RGPs and hard contact lenses, may be made of any suitable material or combination of materials and may have any suitable configuration. The invention is also applicable to preserving compositions, such as contact lens care compositions and other eye care products, which are benefited by being preserved.

One important feature of the compositions of the present invention is the inclusion of an effective, e.g., for disinfecting and/or preserving, amount of at least one ophthalmically acceptable quaternary ammonium substituted matrix material, hereinafter referred to as QASM. The matrix material is selected from proteinaceous materials, carbohydrate materials and mixtures thereof. Without wishing to limit the invention to any particular theory of operation, it is believed that the quaternary ammonium substituents are present in sufficient quantity to effectively provide the desired disinfecting or preserving activity. Further, it is believed that the matrix material is such as to be not substantially adsorbed onto nor absorbed into the lens during the time the lens is contacted with the composition. Thus, the desired disinfecting or preserving is effected substantially without the disinfectant or preservative contaminating the lens which it contacts.

The presently useful QASMs are distinguished from the quaternary ammonium polymers described in Stark U.S. Pat. No. 4,525,346. In Stark, the quaternary ammonium groups are actually part of the polymer backbone. The quaternary ammonium groups of the presently useful disinfectants and preservatives are substituents on a matrix material backbone. The character or nature of the matrix material is such that the present disinfectants or preservatives provide the desired antimicrobial activity without causing substantial eye irritation and sensitivity. In addition, the degree of quaternary ammonium group substitution can be adjusted, as desired, to suit the antimicrobial activity requirements of the particular application involved.

The QASM is preferably dispersible or soluble in the ophthalmically acceptable medium. Since contact lens disinfecting, preserving and other care compositions are most often solutions, the QASM is more preferably soluble in the medium. The amount of QASM employed in the present compositions is that sufficient to effect the desired result. Care should be taken to avoid excessive amounts of QASM. Not only are such materials quite expensive, but the use of large excesses of QASM may result in some degree of eye irritation and/or sensitivity. The presently useful QASMs are preferably present in an amount in the range of about 0.00001% to about 1%, more preferably about 0.0001% to about 0.5%, by weight per volume of ophthalmically acceptable medium.

As noted above, the matrix material substituted with quaternary ammonium groups is selected from proteinaceous materials, carbohydrate materials and mixtures thereof. In one particularly useful embodiment, the matrix material is selected from polypeptides and mixtures thereof. When the matrix material is polypeptide-based, the QASM preferably has a molecular weight in the range of about 500 to about 5000.

A useful quaternary ammonium substituted matrix material has the formula

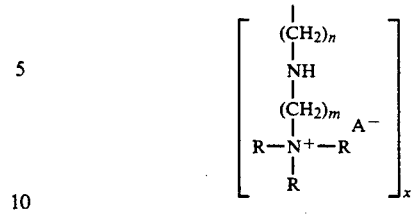

wherein the wavy line represents a polypeptide backbone; n is an integer in the range of 1 to about 5, preferably 2; m is an integer in the range of 1 to about 30, preferably about 10 to about 20; each R is independently selected from alkyl groups containing 1 to about 20 carbon atoms; $A^-$ is selected from ophthalmically acceptable anions; and x represents the number of bracketed groups interspersed along the polypeptide backbone and is an integer in the range of 1 to about 20, preferably about 2 to about 6. In one embodiment, at least one R is methyl and one other R contains about 8 to about 20 carbon atoms. In another embodiment, each of the Rs is methyl, and m is in the range of about 10 to about 20.

Examples of ophthalmically acceptable anions include chloride ($Cl^-$), bromide, iodide, sulfate, bisulfate, phosphate, acid phosphate, nitrate, acetate, maleate, fumarate, oxalate, lactate, tartrate, citrate, gluconate, saccharate, p-toluene sulfonate and the like. The preferred ophthalmically acceptable anion is $Cl^-$.

Examples of the quaternary ammonium substituted polypeptides useful in the present invention are those materials, commonly known as "polyquats" which are based on a collagen hydrolysate of relatively low molecular weight. Such materials are sold by Croda, Inc. under the trademark Croquat L (for a material which includes lauryl trimethyl ammonium chloride groups) and Croquat S (for a material which includes stearyl trimethyl ammonium chloride groups). Such materials are known to be useful as foamers in hair shampoos.

Any suitable quaternary ammonium substituted carbohydrate material may be employed in the present invention provided that it functions as described herein. In a useful embodiment, the quaternary ammonium substituted carbohydrate material has a molecular weight, e.g., an average molecular weight, in the range of about 50,000 to about 200,000. Cellulosic materials are particularly useful carbohydrate-based matrix materials, with hydroxyethyl cellulose being particularly useful.

Examples of quaternary ammonium substituted carbohydrate materials useful in the present invention are those materials, in particular hydroxyethyl cellulose, quaternised with alkyl fatty quaternary ammonium groups. Included among such materials are those sold by Croda, Inc. under the trademark Crodacel QL (for a material in which the quaternary ammonium group includes a lauryl group), Crodacel QM (for a material in which the quaternary ammonium group includes a cocyl group) and Crodacel QS (for a material in which the quaternary ammonium group includes a stearyl group). Such materials are known for use as conditioners for hair care and skin care products.

In addition to one or more QASMs, the present compositions preferably include a water-soluble quaternary ammonium polymer, hereinafter referred to as WQAP. Such polymers are present in an amount effective to at east promote the action of the QASMs as disinfectants and/or preservatives. Thus, it has been found that the presence of a WQAP compliments or enhances the disinfecting and/or preserving obtained using the QASMs in the present invention. The amount of WQAP present is preferably in the range of about 0.00001% to about 1%, more preferably about 0.0001% to about 0.5% by weight per volume of ophthalmically acceptable medium.

Particularly useful WQAPs include amineepichlorohydrin polymers, ionene polymers and mixtures thereof. Such polymers and methods for their production are described in Buckman et al U.S. Pat. No. 4,250,269, which patent is hereby incorporated in its entirety herein by reference. A specific example of a WQAP useful in the present invention is poly (oxyethylene (dimethyliminio) ethylene(dimethyliminio) ethylene dichloride), such as that sold by Buckman Laboratories, Inc. under the trademark WSCP. Another specific WQAP useful in the present invention is (1,5-dimethyl-1,5-diazaundecamethylene polymethobromide, hexadimethrine bromide), sold by Aldrich Chemical Company 20 under the trademark Polybrene.

The present compositions may include other, e.g., complementary and/or potentiating, antimicrobial agents. Examples of such other antimicrobial agents include, but are not limited to, thimerosal, sorbic acid, 1.5-pentanedial, alkyl triethanolamines, boric acid, ophthalmically acceptable salts of any of the above, 3-chloroallyl-3, 5, 7, triaza-1-azonia adamantine chloride, phenylmercuric salts and mixtures thereof. Ophthalmically acceptable salts may include one or more ophthalmically acceptable anions, e.g., as noted above, or ophthalmically acceptable cations, in particular alkali and alkali metal cations. Materials which provide more than one beneficial or desired property to the present compositions may also be included. For example, certain combinations of quaternary ammonium compounds which possess both antimicrobial activity and wetting properties may be included. Examples of such combinations of quaternary ammonium compounds include, but are not limited to, balanced mixtures of N-alkyl dimethyl benzyl ammonium chlorides and N-alkyl dimethyl ethylbenzyl ammonium chlorides. Each of these agents/materials may be included in the present compositions in an amount effective to provide the beneficial or desired property or properties.

The compositions of the present invention include an ophthalmically acceptable medium, preferably an ophthalmically acceptable liquid aqueous medium. This medium often acts as a carrier, e.g., as a solvent, for the other components in the composition. A material is "ophthalmically acceptable" if the material can be placed into a mammalian eye without causing any substantial damage or harm to the eye. One particularly useful ophthalmically acceptable medium is water. Preferably, the medium, and in fact the entire composition, is sterile.

One or more additional components can be included in the present compositions based on the particular application for which the compositions are formulated. Thus, the present compositions can be formulated as disinfecting compositions, cleaning compositions, wetting compositions, conditioning compositions, soaking compositions and the like. Also, the present compositions can be formulated to be useful in performing two or more contact lens caring operations. For example, a disinfecting/cleaning composition, or a cleaning/conditioning composition or even an all purpose lens care composition can be formulated and such multi-functional compositions are included within the scope of the present invention.

The additional component or components included in the present compositions are chosen to impart or provide at least one beneficial or desired property to the compositions. Such additional components may be selected from components which are conventionally used in one or more contact lens care compositions. Examples of such additional components include buffering agents, cleaning agents, wetting agents, sequestering agents, viscosity builders, tonicity agents, nutrient agents, contact lens conditioning agents, antioxidants, pH adjustors, and the like. These additional components are each included in the present compositions in an amount effective to impart or provide the beneficial or desired property to the compositions. For example, such additional components may be included in the present compositions in amounts similar to the amounts of such components used in other, e.g., conventional, contact lens care products.

Useful buffering agents include, but not limited to, acetate buffers, citrate buffers, phosphate buffers and borate buffers. Acids and bases may be used to adjust the pH of the present compositions as needed.

Useful wetting agents include, but are not limited to, polyvinyl alcohol, polyoxamers, polyvinyl pyrrolidone, hydroxypropyl methyl cellulose and mixtures thereof.

Useful sequestering agents include, but are not limited to, disodium ethylene diamine tetraacetate, alkali metal hexametaphosphate, citric acid, sodium citrate and mixtures thereof.

Useful tonicity adjustors include, but are not limited to, sodium chloride, potassium chloride, mannitol, dextrose, glycerin, propylene glycol and mixtures thereof.

Useful viscosity builders include, but are not limited to, hydroxyethyl cellulose, hydroxypropyl methyl cellulose, polyvinyl pyrrolidone, polyvinyl alcohol and mixtures thereof.

Useful antioxidants include, but are not limited to, sodium metabisulfite, sodium thiosulfate, N-acetylcysteine, butylated hydroxyanisole, butylated hydroxytouene and mixtures thereof.

In a particularly useful embodiment, the QASM-containing composition further includes at least one enzyme effective to remove debris from a contact lens. Among the types of debris that form on a contact lens during normal use are protein-based debris, mucin-based debris, lipid-based debris and carbohydrate-based debris. One or more types of debris may be present on a single contact lens.

The enzyme employed may be selected from enzymes which are conventionally employed in the enzymatic cleaning of contact lenses. For example, many of the enzymes disclosed in Huth et al U.S. Pat. No. 32,672 and Karageozian et al U.S. Pat. No. 3,910,296 are useful in the present invention. Each of these patents is incorporated in its entirety by reference herein. Among the useful enzymes are those selected from proteolytic enzymes, lipases and mixtures thereof.

Preferred proteolytic enzymes are those which are substantially free of sulfhydryl groups or disulfide bonds. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Asperigillus molds. Within this grouping, the still more preferred enzymes are the derived alkaline proteases generically called subtilisin enzymes. Reference is made to Deayl, L., Moser, P. W. and Wildi. B. S., "Proteases of the Genus Bacillus". II alkaline Proteases, "Biotechnology and Bioengineering, Vol. XII, pp 213-249 (1970) and Keay, L. and Moser, P. W., "Differentiation of Alkaline Proteases form Bacillus Species" Biochemical and Biophysical Research Comm., Vol 34, No. 5, pp 600-604, (1969).

The subtilisin enzymes are broken down onto two sub-classes, subtilisin A and subtilisin B. In the subtilisin A grouping are enzymes derived from such species as *B. subtilis, B. licheniformis* and *B. pumilis.* Organisms in this sub-class produce little or no neutral protease or amylase. The subtilisin B sub-class is made up of enzymes from such organisms as *B. subtilis, B. subtilis var. amylosacchariticus, B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *B. polymyxa*).

An effective amount of enzyme is to be used in the practice of this invention. Such amount will be that amount which effects removal in a reasonable time (for example about 4 hours to overnight) of substantially all proteinaceous 20 deposits from a lens due to normal wear. This standard is stated with reference to contact lens wearers with a history of normal pattern of protein accretion, not the very small group who may at one time or another have a significantly increased rate of protein deposit such that cleaning is recommended every day, or every two or three days.

The amount of enzyme required to make an effective cleaner will depend on several factors, including the inherent activity of the enzyme, and the excipient it contains.

As a basic yardstick, the working solution should contain sufficient enzyme to provide about 0.001 to about 3 Anson units of activity, preferably about 0.01 to about 1 Anson units, per single lens treatment. Higher or lower amounts may be used.

Enzyme activity is pH dependent. Thus, for any given enzyme, there is a particular pH range in which that enzyme will function best. The determination of such range can readily be done by known techniques.

The present compositions may be used in the care of a contact lens, e.g., to disinfect the lens, to preserve the lens, to otherwise treat the lens and/or to make wearing the lens safe and comfortable. The present compositions, formulated appropriately, may be used in conventional contact lens care regimens by using the present compositions in place of prior conventional compositions. In many instances, these contact lens care regimens involve contacting the lens with the present composition in an amount, and at conditions, effective to obtain the beneficial or desired contact lens care result. For example, a contact lens to be disinfected may be contacted with a disinfecting composition, e.g., aqueous solution, according to the present invention, preferably at a temperature in the range of about 0° C. to about 100° C., more preferably in the range of about 10° C. to about 60° C. and still more preferably in the range of about 15° C. to about 30° C. Contacting at or about ambient temperature is very convenient and useful. The contacting preferably occurs at or about atmospheric pressure. The contacting preferably occurs for a time to substantially disinfect the lens being treated. Such contacting times can be in the range of about 1 minute to about 12 hours or more.

After this contacting, the disinfected contact lens can be taken from the composition and placed directly in an eye, e.g., a human eye, for safe and comfortable wear. Alternately, after being disinfected, the contact lens can be contacted with a second medium, e.g., a liquid aqueous medium such as a preserved isotonic saline solution, prior to being placed in the eye of the wearer of the disinfected contact lens.

The contact lens care compositions disclosed herein are adaptable for use in most types of contact lens care equipment, such as ultrasonic cleaners and the like.

The following examples are set out to illustrate, but not limit, the scope of this invention.

EXAMPLES 1 TO 4

A series of four (4) compositions were prepared by blending the constituents together. These compositions were as follows:

| CONSTITUENT | COMPOSITION[5] | | | |
|---|---|---|---|---|
| | 1 | 2 | 3 | 4 |
| Quaternary ammonium[1] substituted polypeptide, wt. % | 0.01 | 0.001 | 0.005 | 0.005 |
| Water-soluble quaternary[2] ammonium polymer, wt. % | 0.006 | 0.001 | 0.006 | |
| Disodium ethylene diamine tetraacetate, wt. % | 0.127 | | 0.10 | 0.05 |
| Sodium chloride, wt. % | 0.67 | 0.08 | 0.60 | 0.60 |
| Boric acid, wt. % | 0.39 | | 0.39 | 0.39 |
| Sodium Borate Decahydrate NF, Wt. % | 0.2 | 0.132 | 0.2 | 0.2 |
| Nonionic surfactant[3] wt. % | | | 0.1 | 0.01 |
| Hydroxyethyl cellulose NF, wt. % | 0.65 | | | |
| Polyvinylpyrrolidone USP, wt. % | | | | 0.5 |
| Polyethylene glycol 300 NF, wt. % | | 3.0 | | |
| Polyoxyl 40 stearate, wt. % | | 0.5 | | |
| Sodium acetate (trihydrate) USP, wt. % | | 0.498 | | |
| Sodium citrate (dihydrate) USP, wt. % | | 0.132 | | |
| Dextrose monohydrate, wt. % | | 0.06 | | |
| Potassium chloride, wt. % | | 0.0456 | | |
| Calcium chloride (dehydrate) USP, wt. % | | 0.0216 | | |
| Magnesium chloride hexahydrate USP, wt. % | | 0.018 | | |
| pH Range | 7.4 – 7.6 | 7.3 – 7.5 | 7.3 – 7.5 | 7.3 – 7.5 |

-continued

| CONSTITUENT | COMPOSITION[5] | | | |
|---|---|---|---|---|
| | 1 | 2 | 3 | 4 |
| Purified water, USP | QS | QS | QS | QS |

[1] An aqueous solution containing 50% by weight of a quaternary ammonium substituted polypeptide having a molecular weight of about 2500. This material, which includes lauryl trimethyl ammonium chloride groups covalently bonded to the polypeptide chain through amino groups, is sold under the trademark CROQUAT L by Croda, Inc.
[2] A concentrate containing 60% by weight of poly(oxyethylene(dimethyliminio) ethylene-(dimethyliminio) ethylene dichloride) sold under the trademark WSCP by Buckman Laboratories, Inc.
[3] A nonionic surfactant containing polyoxyethylene-polyoxypropylene block copolymer and sold under the trademark Pluronic F 127 by BASF Wyandotte Corporation.
[4] In Compositions 1, 3, and 4, hydrochloric acid and sodium hydroxide were added to give a pH within the range indicated. In Composition 2, glacial acetic acid was used.
[5] Composition 1 was formulated as a rigid gas permeable contact lens soaking and disinfecting solution. Composition 2 was formulated as in-the-eye cleaning and rewetting nutrient drops. Compositions 3 and 4 were formulated as disinfecting solutions for hydrogel soft contact lenses.

Each of these compositions was tested, following the standard procedure, to determine the D-value with respect to various microorganisms The D-value is defined as the length of time required to reduce the microbial burden or load by one log unit.

Results of these tests were as follows:

| | Extrapolated D-Value at 23 C., min. Composition | | | |
|---|---|---|---|---|
| Microorganism | 1 | 2 | 3 | 4 |
| S. marcescens | <64 | — | <170 | <120 |
| S. aureus | <62 | <150 | <72 | <109 |
| P. aeruginosa | <60 | <95 | <65 | <65 |
| E. coli | <63 | <133 | <120 | <106 |
| C. albicans | <150 | <3360 | <156 | <156 |

All of these compositions were tested for preservative efficacy and passed the USP preservative efficacy criteria.

These results demonstrate that quaternary ammonium substituted polypeptides at concentrations ranging from 0.0005% to about 0.005%, by weight, are effective antimicrobial preservatives for contact lens care products. The inclusion of a water-soluble quaternary ammonium polymer, such as in Compositions 1, 2 and 3, increases the antimicrobial activity of the composition against certain microorganisms. Compositions 1, 3, and 4 each is quite effective as a contact lens disinfecting solution in a standard contact lens care regimen, with or without simultaneous or sequential enzymatic lens cleaning as part of the regimen. Composition 2 is effectively preserved and is useful when administered as in-the-eye cleaning and rewetting nutrient drops.

EXAMPLE 5

Composition 3, described above, is used to disinfect a conventional hydrogel soft contact lens as follows. 7.5 ml of the composition is provided at room temperature. The contact lens to be disinfected is placed in the composition. Four hours after the contact lens is first introduced into the composition, it is removed from the composition and placed directly into the wearer's eye. It is found that after four hours, the contact lens is effectively disinfected. Also, the lens wearer experiences no discomfort or eye irritation from. wearing the disinfected contact lens. Alternately, after the contacting for four hours noted above, the disinfected contact lens is rinsed with preserved or non-preserved sterile isotonic saline solution prior to placing the disinfected lens in the wearer's eye. The lens wearer experiences no discomfort or eye irritation from wearing the disinfected contact lens.

EXAMPLE 6

Example 5 is repeated except that about 50 ppm by weight of subtilisin A, based on the total weight of the Composition 4 used, is added at the same time the contact lens to be disinfected is added to the composition. Four hours after the contact lens is first introduced into the composition, it is removed from the composition, rinsed with Composition 3, or preserved or non-preserved sterile isotonic saline solution, and placed directly into the wearer's eye. It is found that after four hours, the contact lens is effectively disinfected and cleaned of protein-based debris. Also, the lens wearer experiences no discomfort or eye irritation from wearing the disinfected and cleaned contact lens.

EXAMPLE 7

Composition 4, described above, is used to disinfect a conventional hydrogel soft contact lens as follows. 7.5 ml of the composition is provided at room temperature. The contact lens to be disinfected is placed in the composition. Four hours after the contact lens is first introduced into the composition, it is removed from the composition and placed directly into the wearer's eye. It is found that after four hours, the contact lens is effectively disinfected. Also, the lens wearer experiences no discomfort or eye irritation from wearing the disinfected contact lens. Alternately, after the contacting for four hours noted above, the disinfected contact lens is rinsed with preserved or non-preserved sterile isotonic saline solution prior to placing the disinfected lens in the wearer's eye. The lens wearer experiences no discomfort or eye irritation from wearing the disinfected contact lens.

EXAMPLE 8

Example 7 is repeated except that about 50 ppm by weight of subtilisin A, based on the total weight of the Composition 4 used, is added at the same time the contact lens to be disinfected is added to the composition. Four hours after the contact lens is first introduced into the composition, it is removed from the composition, washed with Composition 4, or preserved or non-preserved sterile isotonic saline solution, and placed directly into the wearer's eye. It is found that after four hours, the contact lens is effectively disinfected and cleaned of protein-based debris. Also, the lens wearer experiences no discomfort or eye irritation from wearing the disinfected and cleaned contact lens.

EXAMPLES 9-12

A series of compositions similar to Compositions 1 to 4 are prepared. In each case, however, the quaternary ammonium substituted polypeptide is replaced by an equivalent, i.e., in terms of antimicrobial activity, amount of a quaternary ammonium substituted hydroxyethyl cellulose. This material includes lauryl dimethyl ammonium chloride groups. This material is sold under the trademark CRODACEL QL by Croda, Inc. Compositions 9, 10, 11 and 12 correspond to Compositions 1, 2, 3 and 4 respectively.

All of these compositions are tested for preservation efficacy and passes the USP preservative efficacy criteria.

The quaternary ammonium substituted hydroxyethyl cellulose is an effective antimicrobial preservative for contact lens care products. Compositions 9, 11 and 12 each is quite effective as a contact lens disinfecting solution in a standard contact lens care regimen, with or without simultaneous or sequential enzymatic lens cleaning as part of the regimen. Composition 10 is effectively preserved and is useful when administered as in-the-eye cleaning and rewetting nutrient drops.

EXAMPLE 13

Composition 11, described above, is used to disinfect a conventional hydrogel soft contact lens as follows. 7.5 ml of the composition is provided at room temperature. The contact lens to be disinfected is placed in the composition. Four hours after the contact lens is first introduced into the composition, it is removed from the composition and placed directly into the wearer's eye. It is found that after four hours, the contact lens is effectively disinfected. Also, the lens wearer experiences no discomfort or eye irritation from wearing the disinfected contact lens. Alternately, after the contacting for four hours noted above, the disinfected contact lens is rinsed with preserved or non-preserved sterile isotonic saline solution prior to placing the disinfected lens in the wearer's eye. The lens wearer experiences no discomfort or eye irritation from wearing the disinfected contact lens.

EXAMPLE 14

Example 13 is repeated except that about 50 ppm by weight of subtilisin A, based on the total weight of the Composition 11 used, is added at the same time the contact lens to be disinfected is added to the composition. Four hours after the contact lens is first introduced into the composition, it is removed from the composition, rinsed with Composition 11, or preserved or non-preserved sterile isotonic saline solution, and placed directly into the wearer's eye. It is found that after four hours, the contact lens is effectively disinfected and cleaned of protein-based debris. Also, the lens wearer experiences no discomfort or eye irritation from wearing the disinfected and cleaned contact lens.

EXAMPLE 15

Composition 12, described above, is used to disinfect a conventional hydrogel soft contact lens as follows. 7.5 ml of the composition is provided at room temperature. The contact lens to be disinfected is placed in the composition. Four hours after the contact lens is first introduced into the composition, it is removed from the composition and placed directly into the wearer's eye. It is found that after four hours, the contact lens is effectively disinfected. Also, the lens wearer experiences no discomfort or eye irritation from wearing the disinfected contact lens. Alternately, after the contacting for four hours noted above, the disinfected contact lens is rinsed with preserved or non-preserved sterile isotonic saline solution prior to placing the disinfected lens in the wearer's eye. The lens wearer experiences no discomfort or eye irritation from wearing the disinfected contact lens.

EXAMPLE 16

Example 15 is repeated except that about 50 ppm by weight of subtilisin A, based on the total weight of the Composition 12 used, is added at the same time the contact lens to be disinfected is added to the composition. Four hours after the contact lens is first removed from the composition, it is introduced into the composition, rinsed with composition 12, or preserved or non-preserved sterile isotonic saline solution, and placed directly into the wearer's eye. It is found that after four hours, the contact lens is effectively disinfected and cleaned of protein-based debris. Also, the lens wearer experiences no discomfort or eye irritation from wearing the disinfected and cleaned contact lens.

While this invention has been described with respect to various specific examples and embodiments, it is to be understood that the invention is not limited thereto and that it can be variously practiced within the scope of the following claims.

What is claimed is:

1. A method for disinfecting a contact lens comprising:
   contacting a contact lens with an effective disinfecting amount of an ophthamically acceptable quaternary ammonium substituted matrix material, said matrix material being selected from the group consisting of proteinaceous materials, carbohydrate materials and mixtures thereof.

2. The method of claim 1 wherein said contacting occurs in a liquid aqueous medium which includes an effective buffering amount of buffer and said effective disinfecting amount of said quaternary ammonium substituted matrix material is dispersible or soluble in said liquid aqueous medium.

3. The method of claim 2 wherein said liquid aqueous medium is ophthalmically acceptable and includes an effective buffering amount of borate buffer.

4. The method of claim 1 wherein the quaternary ammonium substituent of said quaternary ammonium substituted matrix material includes at least one alkyl group containing 1 to about 6 carbon atoms.

5. The method of claim 2 wherein said quaternary ammonium substituted matrix material is present during said contacting in an amount in the range of about 0.00001% to about 1% by weight per volume f said liquid aqueous medium.

6. The method of claim 2 wherein said contact lens after being disinfected is contacted with a second liquid aqueous medium prior to being placed in the eye of the wearer of said contact lens.

7. The method of claim 1 which further comprises contacting said contact lens in a liquid medium with at least one enzyme capable of removing debris from a contact lens in an amount effective to remove debris from said contact lens.

8. The method of claim 7 wherein said contact lens-quaternary ammonium substituted matrix material contacting and said contact lens-enzyme contacting occur at substantially the same time.

9. The method of claim 1 wherein said matrix material is selected from the group consisting of cellulosic materials and mixtures thereof.

10. The method of claim 1 wherein said matrix material is hydroxyethyl cellulose.

11. The method of claim 9 wherein said quaternary ammonium substituted matrix material has a molecular weight in the range of about 50,000 to about 200,000.

12. The method of claim 1 wherein said matrix material is selected from the group consisting of polypeptides and mixtures thereof.

13. The method of claim 12 where said quaternary ammonium substituted polypeptides have a molecular weight in the range of about 500 to about 5000.

14. The method of claim 1 wherein said quaternary ammonium substituted matrix material has a formula

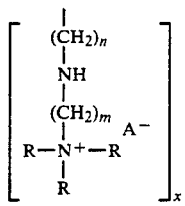

wherein said wavy line is a polypeptide backbone; n is an integer in the range of 1 to about 5; m is an integer in the range of 1 to about 30; each R is independently selected from the group consisting of alkyl groups containing 1 to about 20 carbon atoms; $A^-$ is selected from the group consisting of ophthalmically acceptable anions; and x represents the number of bracketed groups interspersed along said polypeptide backbone and is an integer in the range of 1 to about 20.

15. The method of claim 14 wherein $A^-$ is $Cl^-$.

16. The method of claim 14 wherein at least one R is methyl and one other R contains about 8 to about 20 carbon atoms.

17. The method of claim 14 wherein n is 2, n is in the range of about 10 to about 20, each of the Rs is methyl, and x is about 2 to about 6.

18. The method of claim 1 wherein said contacting occurs in the presence of a water-soluble quaternary ammonium polymer selected from the group consisting of amineepichlorohydrin polymers, ionene polymers and mixtures thereof, said water-soluble quaternary ammonium polymer being present in an amount effective to at least promote the disinfecting of said contact lens.

19. The method of claim 18 wherein said contacting occurs in a liquid aqueous medium and said water-soluble quaternary ammonium polymer is present in an amount in the range of about 0.00001% to about 1% by weight per volume of said liquid aqueous medium.

20. The method of claim 18 wherein said water-soluble quaternary ammonium polymer is poly (oxyethylene (dimethyliminio) ethylene (dimethyliminio) ethylene dichloride).

21. A method of preserving an ophthalmically acceptable medium comprising:
contacting an ophthalmically acceptable medium including an effective buffering amount of buffer with an effective preserving amount of an ophthalmically acceptable quaternary ammonium substituted matrix material, said matrix material being selected from the group consisting of proteinaceous materials, carbohydrate materials and mixtures thereof.

22. The method of claim 21 wherein said ophthalmically acceptable medium is a liquid aqueous medium and is useful in caring for a contact lens and said quaternary ammonium substituted matrix material is dispersible or soluble in said ophthalmically acceptable medium.

23. The method of claim 22 wherein said ophthalmically acceptable medium is sterile.

24. The method of claim 21 wherein said ophthalmically acceptable medium is a liquid aqueous medium and includes an effective buffering amount of borate buffer.

25. The method of claim 21 wherein the quaternary ammonium substituent of said quaternary ammonium substituted matrix material includes at least one alkyl group containing 1 to about 6 carbon atoms.

26. The method of claim 21 wherein said quaternary ammonium substituted matrix material is present during said contacting in an amount in the range of about 0.00001% to about 1% by weight per volume of said ophthalmically acceptable medium.

27. The method of claim 21 wherein said matrix material is selected from the group consisting of cellulosic materials and mixtures thereof.

28. The method of claim 21 wherein said matrix material is hydroxyethyl cellulose.

29. The method of claim 24 wherein said matrix material is selected from the group consisting of polypeptides and mixtures thereof.

30. The method of claim 21 wherein said quaternary ammonium substituted matrix material has a formula

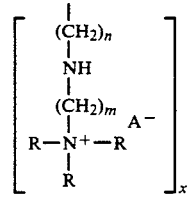

wherein said wavy line is a polypeptide backbone; n is an integer in the range of 1 to about 5; m is an integer in the range of 1 to about 30; each R is independently selected from the group consisting of alkyl groups containing 1 to about 20 carbon atoms; $A^-$ is selected from the group consisting of ophthalmically acceptable anions; and x represents the number of bracketed groups interspersed along said polypeptide backbone and is an integer in the range of 1 to about 20.

31. The method of claim 30 wherein $A^-$ is $Cl^-$.

32. The method of claim 30 wherein at least one R is methyl and one other R contains about 8 to about 20 carbon atoms.

33. The method of claim 30 wherein n is 2, m is in the range of about 10 to about 20, each of the Rs is methyl and x is about 2 to about 6.

34. The method of claim 21 wherein said contacting occurs in the presence of a water-soluble quaternary ammonium polymer selected from the group consisting of amineepichlorohydrin polymers, ionene polymers and mixtures thereof, said water-soluble quaternary ammonium polymer being present in an amount effective to at least promote the preserving of said ophthalmically acceptable medium.

35. The method of claim 34 wherein said water-soluble quaternary ammonium polymer is present in an amount in the range of about 0.00001% to about 1% by weight per volume of said ophthalmically acceptable medium.

36. The method of claim 34 wherein said water-soluble quaternary ammonium polymer is poly (oxyethylene (dimethyliminio) ethylene (dimethyliminio) ethylene dichloride).

37. A composition useful for disinfecting a contact lens comprising an ophthalmically acceptable, liquid aqueous medium and, included therein, an effective buffering amount of buffer and an effective disinfecting amount o an ophthalmically acceptable quaternary ammonium substituted matrix material, said matrix material being selected from the group consisting of proteinaceous materials, carbohydrate materials and mixtures thereof.

38. The composition of claim 37 wherein said composition is sterile, and said effective, disinfecting amount of said quaternary ammonium substituted matrix material is dispersible or soluble in said ophthalmically acceptable, liquid aqueous medium.

39. The composition of claim 37 wherein the quaternary ammonium substituent of said quaternary ammonium substituted matrix material includes at least one alkyl group containing 1 to about 6 carbon atoms.

40. The composition of claim 37 wherein said quaternary ammonium substituted matrix material is present in an amount in the range of about 0.00001% to about 1% by weight per volume of said ophthalmically acceptable liquid aqueous medium and said composition includes an effective buffering amount of borate buffer.

41. The composition of claim 37 which further comprises at least one enzyme capable of removing debris from a contact lens in an amount effective to remove debris from a protein-based debris laden contact lens.

42. The composition of claim 37 wherein said matrix material is selected from the group consisting of cellulosic materials and mixtures thereof.

43. The composition of claim 37 wherein said matrix material is hydroxyethyl cellulose.

44. The composition of claim 37 wherein said matrix material is selected from the group consisting of polypeptides and mixtures thereof.

45. The composition of claim 44 wherein said quaternary ammonium substituted matrix material has a formula

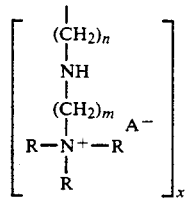

wherein said wavy line is a polypeptide backbone; n is an integer in the range of 1 to about 5; m is an integer in the range of 1 to about 30; each R is independently selected from the group consisting of alkyl groups containing 1 to about 20 carbon atoms; $A^-$ is selected from the group consisting of ophthalmically acceptable anions; and x represents the number of bracketed groups interspersed along said polypeptide backbone and is an integer in the range of 1 to about 20.

46. The composition of claim 45 wherein $A^-$ is $Cl^-$.

47. The composition of claim 45 wherein at least one R is methyl and one other R contains about 8 to about 20 carbon atoms.

48. The composition of claim 45 wherein n is 2, m is in the range of about 10 to about 20, each of the Rs is methyl and x is about 2 to about 6.

49. The composition of claim 37 which further comprises a water-soluble quaternary ammonium polymer selected from the group consisting of amine-epichlorohydrin polymers, ionene polymers and mixtures thereof, said water-soluble quaternary ammonium polymer present in an amount effective to at least promote the disinfecting of a contact lens.

50. The composition of claim 49 wherein said water-soluble quaternary ammonium polymer is present in an amount in the range of about 0.00001% to about 1% by weight per volume of said ophthalmically acceptable liquid aqueous medium.

51. The composition of claim 49 wherein said water-soluble quaternary ammonium polymer is poly (oxyethylene (dimethyliminio) ethylene (dimethyliminio) ethylene dichloride).

52. A preserved composition comprising an ophthalmically acceptable medium and, included therein, an effective buffering amount of buffer and an effective preserving amount of an ophthalmically acceptable quaternary ammonium substituted matrix material, said matrix material being selected from the group consisting of proteinaceous materials, carbohydrate materials and mixtures thereof.

53. The composition of claim 52 wherein said composition is sterile and said ophthalmically acceptable medium is a liquid aqueous medium and is useful in caring for a contact lens.

54. The composition of claim 52 wherein said ophthalmically acceptable medium is a liquid aqueous medium and said quaternary ammonium substituted matrix material is dispersible or soluble in said liquid aqueous medium, and said composition includes an effective buffering amount of borate buffer.

55. The composition of claim 52 wherein the quaternary ammonium substituent of said quaternary ammonium substituted matrix material includes at least one alkyl group containing 1 to about 6 carbon atoms.

56. The composition of claim 52 wherein said quaternary ammonium substituted matrix material is present during said contacting in an amount in the range of about 0.00001% to about 1% by weight per volume of said ophthalmically acceptable medium.

57. The composition of claim 52 wherein said matrix material is selected from the group consisting of cellulosic materials and mixtures thereof.

58. The composition of claim 52 wherein said matrix material is hydroxyethyl cellulose.

59. The composition of claim 52 wherein said matrix material is selected from the group consisting of polypeptides and mixtures thereof.

60. The composition of claim 52 wherein said quaternary ammonium substituted matrix material has a formula

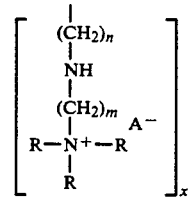

wherein said wavy line is a polypeptide backbone; n is an integer in the range of 1 to about 5; m is an integer in the range of 1 to about 30; each R is independently selected from the group consisting of alkyl groups containing 1 to about 20 carbon atoms; $A^-$ is selected from the group consisting of ophthalmically acceptable anions; and x represents the number of bracketed groups interspersed along said polypeptide backbone and is an integer in the range of 1 to about 20.

61. The composition of claim 60 wherein $A^-$ is $Cl^-$.

62. The composition of claim 60 wherein at least one R is methyl and one other R contains about 8 to about 20 carbon atoms.

63. The composition of claim 60 n is 2, m is in the range of about 10 to about 20, each of the Rs is methyl and x is about 2 to about 6.

64. The composition of claim 52 which further comprises a water-soluble quaternary ammonium polymer selected from the group consisting of amine-epichlorohydrin polymers, ionene polymers and mixtures thereof, said water-soluble quaternary ammonium polymer being present in an amount effective to at least promote the preserving of said ophthalmically acceptable medium.

65. The composition of claim 64 wherein said water-soluble quaternary ammonium polymer is present in an amount in the range of about 0.0001% to about 1% by weight per volume of said ophthalmically acceptable medium.

66. The composition of claim 64 wherein said water-soluble quaternary ammonium polymer is poly (oxyethylene (dimethyliminio) ethylene (dimethyliminio) ethylene dichloride).

* * * * *

UNITED STATES PATENT AND TRADEMARK OFFICE
CERTIFICATE OF CORRECTION

PATENT NO. : 5,171,526
DATED : December 15, 1992
INVENTOR(S) : Wong et al

It is certified that error appears in the above-indentified patent and that said Letters Patent is hereby corrected as shown below:

```
Column 2, line 62; delete "al" and insert in place thereof --all--
Column 4, line 2; insert --           -- (over formula)
Column 4, line 15; delete "20:" and insert in place thereof
    --20;--
Column 5, line 23; after "Company" delete --20--
Column 6, line 56; after "Pat." insert --RE--
Column 7, line 33; after "proteinaceous" delete --20--
Column 8, lines 41 to 43; delete
    "tetracetate, wt. %    0.67   0.08   0.60   0.60
     Sodium chloride,wt.% 0.39           0.39   0.39
     Boric acid, wt. %                                "
and insert in place thereof
   --tetracetate, wt. %
     Sodium chloride,wt.% 0.67   0.08   0.60   0.60
     Boric acid, wt. %    0.39           0.39   0.39--
```

UNITED STATES PATENT AND TRADEMARK OFFICE
CERTIFICATE OF CORRECTION

PATENT NO. : 5,171,526
DATED : December 15, 1992
INVENTOR(S) : Wong et al

It is certified that error appears in the above-indentified patent and that said Letters Patent is hereby corrected as shown below:

```
Column 12, line 40; delete "f" and insert in place thereof --of--
Column 13, line 4; insert --  ⌢  -- (over formula)
Column 14, line 21; insert --  ⌢  -- (over formula)
Column 14, line 68; delete " amount o " and insert in place
   thereof -- amount of --
Column 15, line 37; insert --  ⌢  -- (over formula)
Column 16, line 50; insert --  ⌢  -- (over formula)
Column 17, line 4; after "60" insert --wherein--
```

Signed and Sealed this

Twenty-sixth Day of October, 1993

Attest:

BRUCE LEHMAN

Attesting Officer

Commissioner of Patents and Trademarks